(12) United States Patent
Othman et al.

(10) Patent No.: US 7,413,883 B2
(45) Date of Patent: Aug. 19, 2008

(54) ENANTIOSELECTIVE IMMOBILIZED LIPASE

(75) Inventors: Siti Salhah Othman, Selangor Darul Ehsan (MY); Mahiran Basri, Selangor Darul Ehsan (MY); Halila Jasmani, Selangor Darul Ehsan (MY); Mohd. Zobir Hussein, Selangor Darul Ehsan (MY); Mohd. Basyaruddin Abd. Rahman, Selangor Darul Ehsan (MY); Abu Bakar Salleh, Selangor Darul Ehsan (MY); Raja Noor Zaliha Abd. Rahman, Selangor Darul Ehsan (MY)

(73) Assignee: Universiti Putra Malaysia, Selangor Darul Ehsan (MY)

( * ) Notice: Subject to any disclaimer, the term of this patent is extended or adjusted under 35 U.S.C. 154(b) by 331 days.

(21) Appl. No.: 11/058,189

(22) Filed: Feb. 16, 2005

(65) Prior Publication Data

US 2005/0196850 A1    Sep. 8, 2005

(30) Foreign Application Priority Data

Feb. 18, 2004    (MY) ............................. PI 2004 0529

(51) Int. Cl.
    *C12P 7/40*    (2006.01)
    *C12P 7/62*    (2006.01)
    *C12P 7/02*    (2006.01)
    *C12P 41/00*   (2006.01)
    *C12N 11/14*   (2006.01)
    *C12N 11/08*   (2006.01)

(52) U.S. Cl. ................. 435/136; 435/135; 435/155; 435/176; 435/180; 435/280

(58) Field of Classification Search .................. None
    See application file for complete search history.

(56) References Cited

U.S. PATENT DOCUMENTS

| 4,898,822 | A | * | 2/1990 | Asada et al. | ................ 435/121 |
| 5,108,916 | A | * | 4/1992 | Cobbs et al. | ................ 435/135 |
| 7,192,731 | B2 | * | 3/2007 | Kanner et al. | ................ 435/19 |

* cited by examiner

*Primary Examiner*—David M Naff
(74) *Attorney, Agent, or Firm*—Birch, Stewart Kolasch & Birch, LLP

(57) ABSTRACT

Immobilization of *Candida rugosa* lipase on a carrier selected from the group consisting of macroporous adsorbent resin of the acrylic type, synthetic epoxy activated resin and Mg—Al-hydrotalcite enhances its enantioselectivity by six to seven folds. The immobilized *Candida rugosa* lipase is suitable for use in resolution of racemic alcohols and/or carboxylic acids, particularly in resolution of racemic menthol or production of menthyl esters.

3 Claims, 5 Drawing Sheets

ENANTIOSELECTIVE IMMOBILIZED LIPASE

FIELD OF INVENTION

The present invention relates to immobilized lipase. More particularly, this invention relates to enantioselective immobilized lipase.

BACKGROUND OF THE INVENTION

The demand for enantiomerically pure pharmaceuticals, agrochemicals, and food additives is increasing due to the fact that different forms of enantiomers often have different behavior and can cause different biological effects.

Lipases are most useful in the preparation of enantiomerically pure compounds because lipase is comparatively economical and the lipase catalyzed process can be scaled up.

Although a large number of lipases have been evaluated for resolution of racemic alcohols and/or carboxylic acids, they have not generally met with great success due to low enantiospecificities. Various methodologies have been described to increase the enantioselectivity of lipase in resolution of racemates and immobilization of lipase is one of the methodologies.

U.S. Pat. No. 5,156,963 reports that immobilization of lipase on macroporous adsorbent resin of the acrylic type leads to a product with higher interesterification activity than prior art methods.

U.S. Pat. No. 5,445,955 reports that lipase or phospholipase immobilized on a macroporous adsorbent resin having an epoxy group on the surface thereof exhibits an excellent lipase activity, which is suitable for use for transesterification reaction in a system containing very small amount of water.

The above mentioned U.S. patents do not discuss about the enantioselectivity of the immobilized lipase.

SUMMARY OF THE INVENTION

Immobilization of *Candida rugosa* lipase on a carrier selected from the group consisting of macroporous adsorbent resin of the acrylic type, synthetic epoxy activated resin and Mg—Al-hydrotalcite enhances its enantioselectivity by six to seven folds. The immobilized *Candida rugosa* lipase is suitable for use in resolution of racemic alcohols and/or carboxylic acids, particularly in resolution of racemic menthol or production of menthyl esters.

DESCRIPTION OF THE INVENTION

The inventors found that immobilization of lipase on macroporous adsorbent resin of the acrylic type or a synthetic epoxy activated resin or Mg—Al-hydrotalcite enhances its enantioselectivity by six to seven folds. The enantioselective immobilized lipase is suitable for use in resolution of racemic alcohol and/or carboxylic acid. Ester of the preferred enantiomer is obtained by using the enantioselective immobilized lipase in catalyzing the esterification reaction. Subsequently, the preferred enantiomer is obtained by hydrolyzing the ester produced.

A preferred embodiment of the current invention is described below with reference to the accompanying drawings, in which:

FIG. 1 is a typical chromatogram obtained from chiral gas chromatography of the product as produced by enantioselective esterification of (±)-mentol with butyric anhydride. Peaks A=hexane, B=internal standard, C=butyric anhydride, D=(±)-menthol, E=(−)-menthyl butyrate, F=(+)-menthyl butyrate. The amount of each enantiomers was estimated by area of peak E and F, recorded and integrated by 3395 Hewlett-Packard Integrator (Avondale, Pa.).

FIG. 2 is a graph showing percentage yield of (−)-menthyl butyrate when native or immobilized *Candida rugosa* lipase was used in catalyzing the production of (−)-menthyl butyrate as affected by organic solvents of different hydrophobicity at 30° C. Control=without enzyme, NL=native lipase, EC=Eupergit® C-lipase, EC250L=Eupergit® C 250 L-lipase, XAD7=Amberlite® XAD7-lipase, HT=Mg—Al-Hydrotalcite-lipase.

Figure 1:
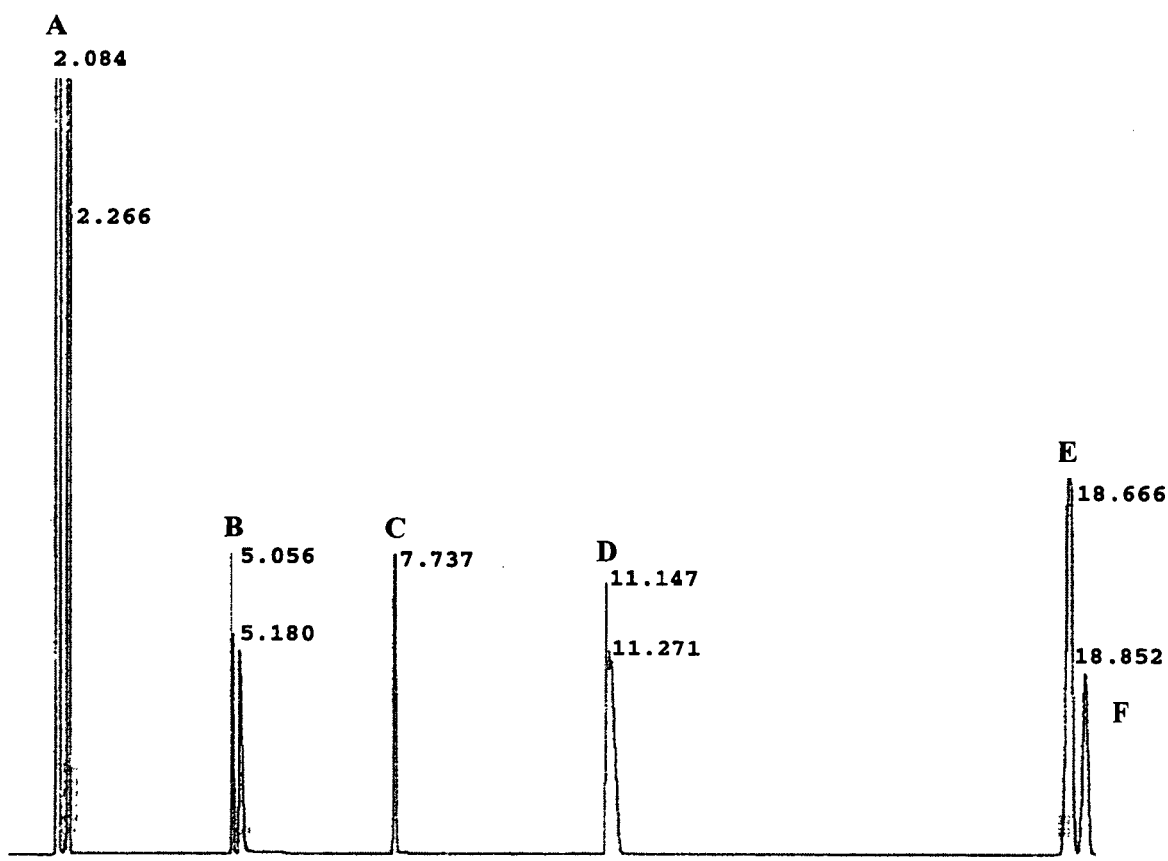
Figure 2:
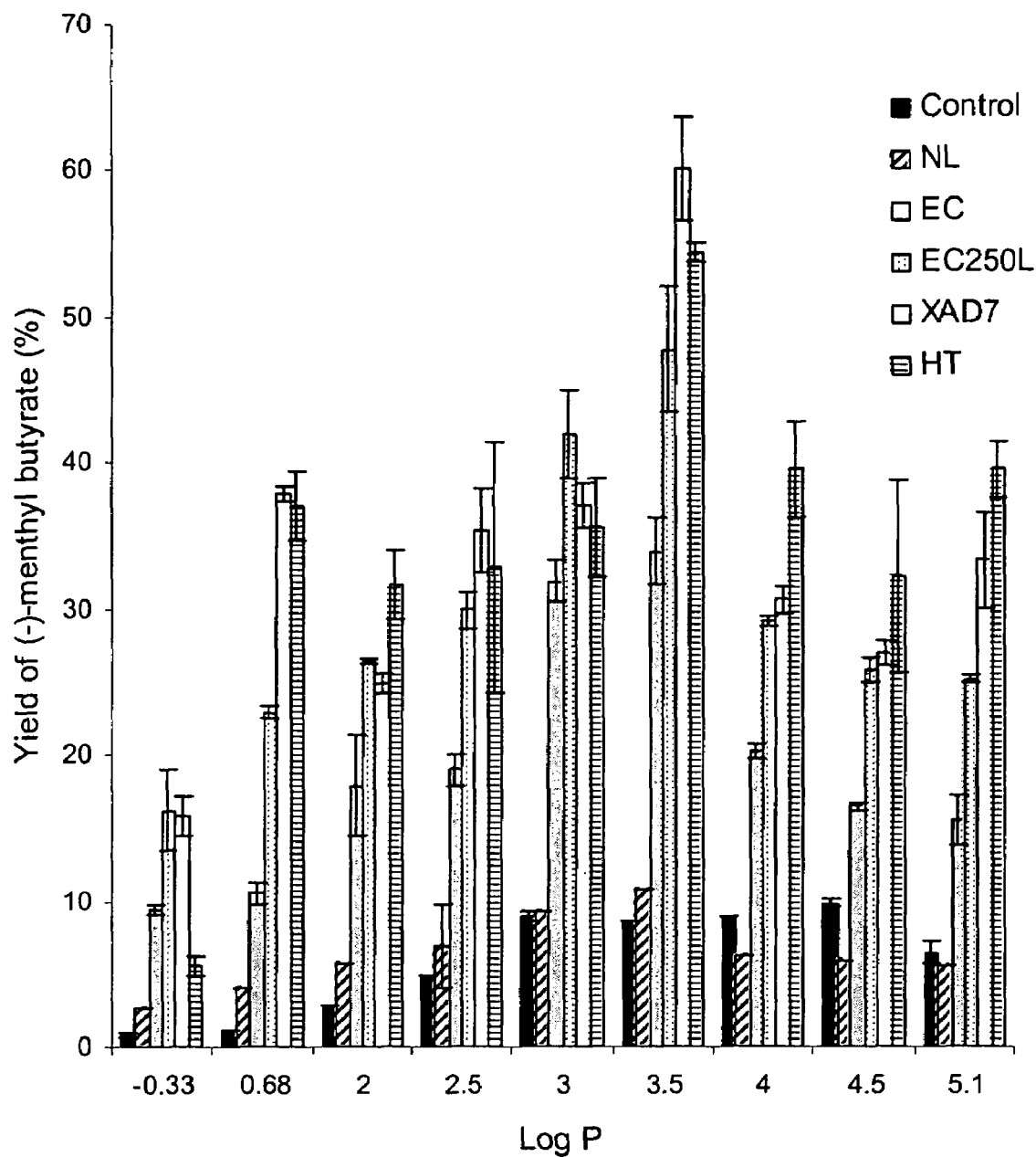
Figure 3:
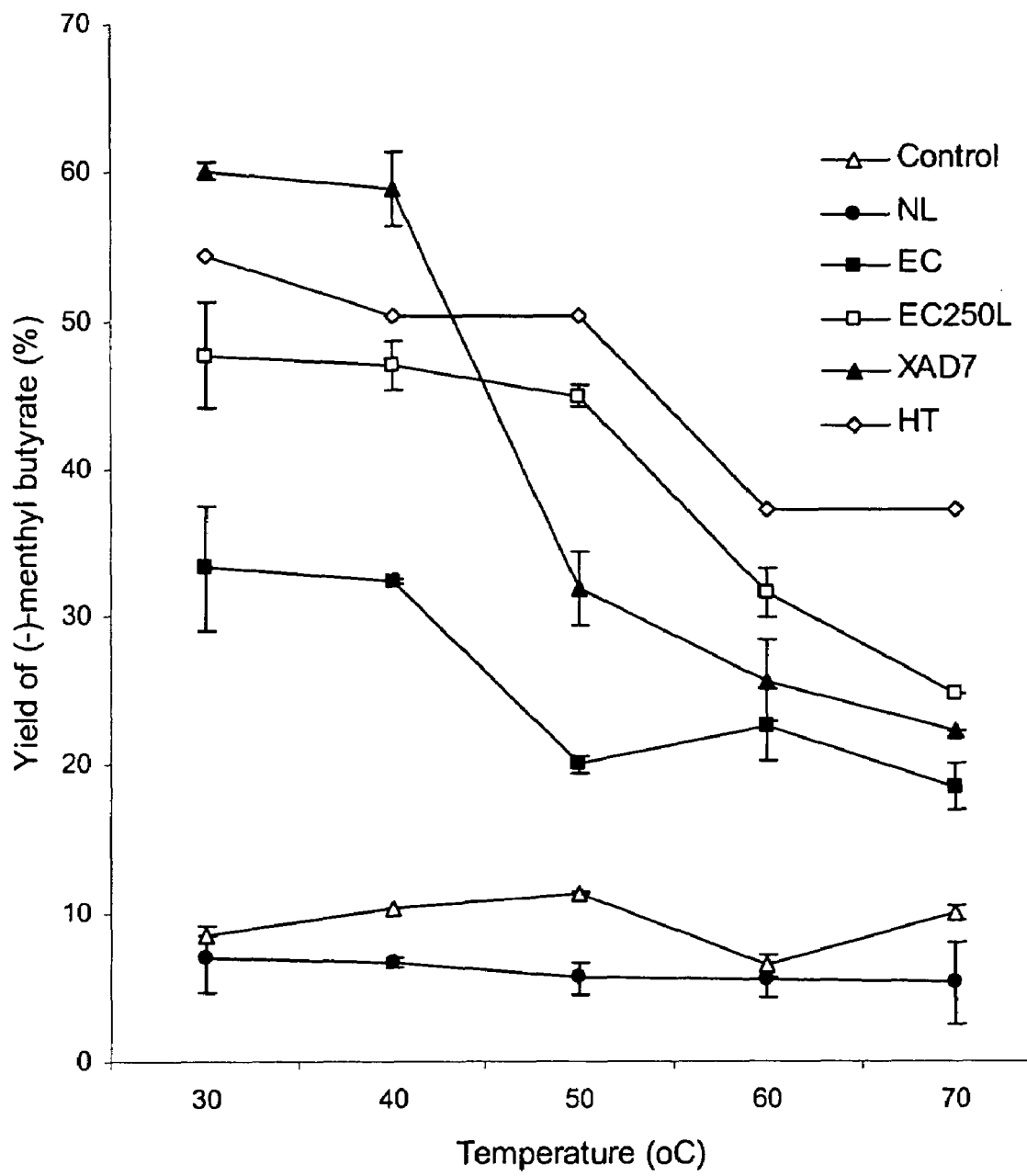
FIG. 3 is a graph showing percentage yield of (−)-menthyl butyrate when native or immobilized *Candida rugosa* lipase was used in catalyzing the production of (−)-menthyl butyrate as affected by reaction temperature. Control=without enzyme, NL=native lipase, EC=Eupergit® C-lipase, EC250L=Eupergit® C 250 L-lipase, XAD7=Amberlite® XAD7-lipase, HT=Mg—Al-Hydrotalcite-lipase.
Figure 4:
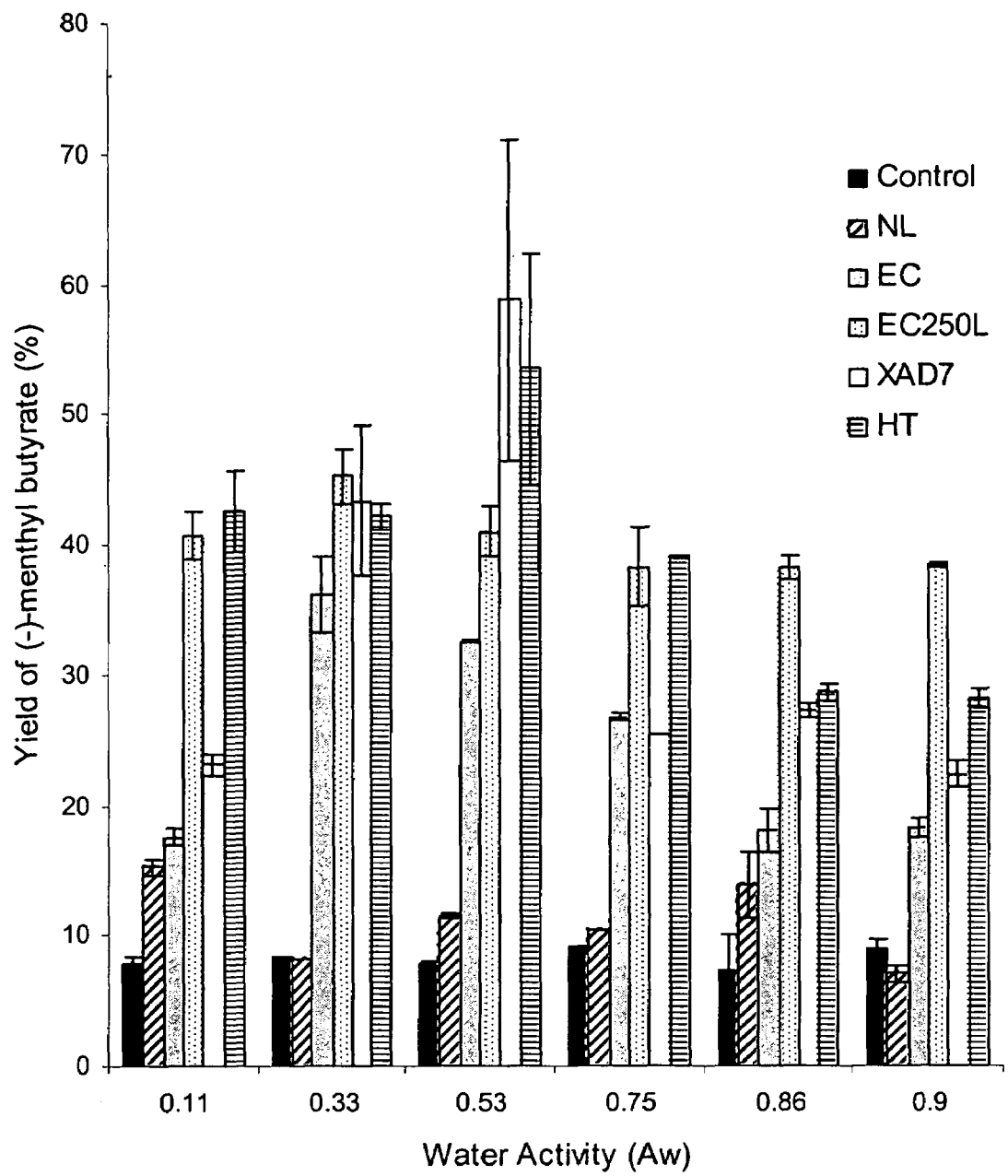
FIG. 4 is a graph showing percentage yield of (−)-menthyl butyrate when native or immobilized *Candida rugosa* lipase was used in catalyzing the production of (−)-menthyl butyrate as affected by water activity at 30° C. Control=without enzyme, NL=native lipase, EC=Eupergit® C-lipase, EC250L=Eupergit® C 250 L-lipase, XAD7=Amberlite® XAD7-lipase, HT=Mg—Al-Hydrotalcite-lipase.
Figure 5:
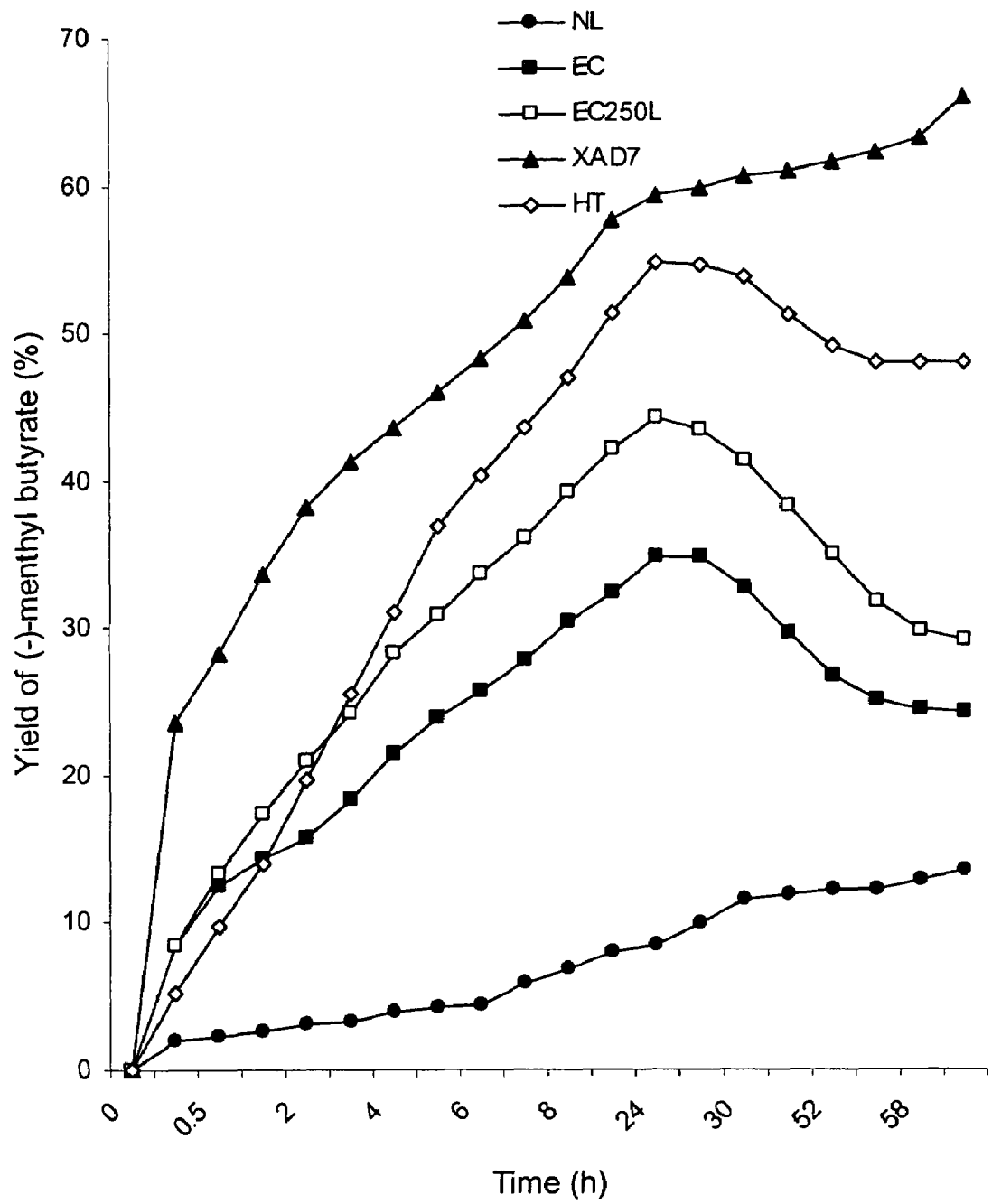
FIG. 5 is a graph showing percentage yield of (−)-menthyl butyrate when native or immobilized *Candida rugosa* lipase was used in catalyzing the production of (−)-menthyl butyrate as affected by reaction period. NL=native lipase, EC=Eupergit® C-lipase, EC250L=Eupergit® C 250 L-lipase, XAD7=Amberlite® XAD7-lipase, HT=Mg—Al-Hydrotalcite-lipase.

Lipases were used to catalyze enantioselective esterification of (±)-menthol to produce high enantiomeric excess of (−)-menthyl esters. (−)-Menthol can be subsequently obtained by hydrolyzing the (−)-menthyl esters produced. The acyl donor used in the enantioselective esterification reaction was butyric anhydride.

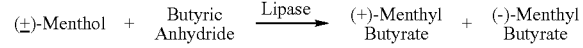

General procedure for conducting the enantioselective esterification reaction unless otherwise stated is forming a reaction mixture which consists of 1:1 molar ratio of (±)-menthol and butyric anhydride in two milliliters hexane, incubating the reaction mixture at 30° C. in a screw-capped vial for twenty four hours with a 150 rpm shaking water bath wherein an amount of free lipase (hereinafter referred to as native lipase) equivalent to approximately 0.5 mg of protein or an amount of immobilized lipase equivalent to approximately 0.4 mg of protein, is added right before incubation.

The percentage yield of (−)-menthyl butyrate is defined as percentage of millimole ester produced per millimole alcohol initially present in the system. The enantioselectivity of lipase is expressed as percentage of enantiomeric excess (ee):

$$\frac{\text{Amount of }(-)\text{-Menthyl Butyrate} - \text{Amount of }(+)\text{-Menthyl Butyrate}}{\text{Total Amount of }(\pm)\text{-Menthyl Butyrate}} \times 100\%$$

Crude commercial lipases from *Aspergillus niger, Candida rugosa, Mucor javanicus, Penicillium roqueforti, Rhizopus niveus, Rhizopus oryzae* and *Rhizopus rhizopodiformis* were screened for their performance in catalyzing the above reaction. The percentage yield of (−)-menthyl butyrate and enantioselectivity of each lipase used are shown in Table 1.

TABLE 1

Performance of lipases from different sources in catalyzing the production of (−)-menthyl butyrate

| Lipase | Yield of (−)-menthyl butyrate (%) | ee (%) |
| --- | --- | --- |
| Aspergillus niger | 5.25 ± 1.21 | 2.49 ± 2.99 |
| Candida rugosa | 8.91 ± 2.67 | 20.79 ± 0.60 |
| Mucor javanicus | 2.53 ± 0.10 | 8.69 ± 0.01 |
| Penicillium roqueforti | 0.89 ± 0.10 | 10.61 ± 0.48 |
| Rhizopus niveus | 7.15 ± 0.09 | 0.56 ± 0.04 |
| Rhizopus oryzae | 10.89 ± 0.23 | 0.70 ± 0.15 |
| Rhizopus rhizopodiformis | 7.53 ± 0.11 | 0.79 ± 0.10 |

The values are reported as means ± standard deviation.

Among the tested lipases, only lipase from *Candida rugosa* gave performance acceptable in terms of reaction rate, percentage yield and optical purity.

Lipase from *Candida rugosa* was immobilized on different carriers to determine carriers which can enhance its performance. Carriers tested include activated carbon, Amberlite® XAD 7 (representative of macroporous adsorbent resin of the acrylic type), Eupergit® C and Eupergit® C 250 L (representatives of synthetic epoxy activated resin), Mg—Al-hydrotalcite, molecular sieves and silica gel. Crude commercial lipase from *Candida rugosa* was purified prior usage. 1.5 g crude commercial *Candida rugosa* lipase was dissolved in 15.0 ml of distilled water. Then, the solution was stirred and centrifuged at 10,000 rpm for 15 minutes. Undissolved solid suspension was discarded after centrifugation whereas the supernatant was used as partially purified lipase or stored at −20° C. prior to use.

The partially purified lipase was added to 2.0 g carrier and the resultant mixture was immersed in a water bath at room temperature while continuously agitated at 100 rpm for 1 hour. Then, the resultant lipase-loaded carrier (immobilized lipase) was separated from residual partially purified lipase and lyophilized in a freeze drier.

Reaction for producing menthyl butyrate was conducted following the general procedure but immobilized lipase on various carriers was used instead of native lipase in catalyzing the reaction. Protein content and amount of each type of lipase used are shown in Table 2 and Table 3. The amount of each native lipase used was equivalent to approximately 0.5 mg of protein while the amount of each immobilized lipase used was equivalent to approximately 0.4 mg of protein. The percentage yield of (−)-menthyl butyrate and enantioselectivity of each immobilized lipase used are shown in Table 4.

TABLE 2

Protein content and amount of native lipases used

| Lipase | [a]Protein Content (mg protein/g lipase) | [b]Amount used (mg) |
| --- | --- | --- |
| Aspergillus niger | 26.3 | 20.15 |
| Candida rugosa | 10.6 | 50.00 |
| Mucor javanicus | 21.3 | 25.02 |
| Penicillium roqueforti | 14.2 | 37.53 |
| Rhizopus niveus | 32.0 | 16.65 |
| Rhizopus oryzae | 19.0 | 28.05 |
| Rhizopus rhizopodiformis | 2.3 | 231.70 |

[a]Protein content was determined using the Bradford (1976) method using bovine serum albumin (BSA) as standard and was determined spectrofotometrically at a wavelength of 595 nm with the calibration curve of BSA.
[b]The amount of each native lipase used was equivalent to approximately 0.5 mg of protein.

TABLE 3

Protein content and amount of immobilized *Candida rugosa* lipase used

| Lipase | [a]Protein Content (mg protein/g carrier) | [b]Amount used (mg) |
| --- | --- | --- |
| Amberlite ® XAD7-lipase | 9.11 | 43.03 |
| Eupergit ® C-lipase | 4.81 | 81.50 |
| Eupergit ® C 250 L-lipase | 11.16 | 35.13 |
| Mg-Al-Hydrotalcite | 3.70 | 105.95 |

[a]Protein content was determined using the Bradford (1976) method using bovine serum albumin (BSA) as standard and was determined spectrofotometrically at a wavelength of 595 nm with the calibration curve of BSA.
[b]The amount of immobilized lipase used was equivalent to approximately 0.4 mg of protein.

TABLE 4

Performance of immobilized *Candida rugosa* lipase on various carriers in catalyzing the production of (−)-menthyl butyrate

| Carrier | Yield of (−)-menthyl butyrate (%) | ee (%) |
| --- | --- | --- |
| Native Lipase | 6.9 ± 0.60 | 13.54 ± 3.23 |
| Activated carbon | 18.66 ± 0.30 | 42.00 ± 1.06 |
| Amberlite ® XAD7 | 58.53 ± 1.87 | 91.96 ± 0.62 |
| Eupergit ® C | 38.35 ± 1.18 | 100.00 ± 0.00 |
| Eupergit ® C 250 L | 48.17 ± 2.10 | 94.79 ± 0.05 |
| Mg-Al-Hydrotalcite | 47.71 ± 3.97 | 80.19 ± 1.97 |
| Molecular sieves | 8.19 ± 0.46 | 2.19 ± 0.20 |
| Silica gel 60 | 24.23 ± 2.76 | 78.81 ± 2.88 |

The values are reported as means ± standard deviation.

Immobilized lipase on activated carbon and molecular sieves produced low enantiomeric excess of (−)-menthyl butyrate. Immobilized lipase on Amberlite® XAD 7, Eupergit® C and Eupergit® C 250 L produced over ninety percent enantiomeric excess of (−)-menthyl butyrate wherein the highest yield of (−)-menthyl butyrate was achieved using Amberlite® XAD 7 as carrier followed by Eupergit® C 250 L and Eupergit® C. Immobilized lipase on Mg—Al-hydrotalcite showed comparable performance in terms of percentage yield and optical purity.

Examples of the effect of various factors on the performance of immobilized lipase in enantioselective esterification of (±)-menthol to produce high enantiomeric excess of (−)-menthyl esters:

EXAMPLE 1

Effect of organic solvents with different hydrophobicity on *Candida rugosa* lipase activity was determined by using the general procedure but substituting hexane with various organic solvents such as acetonitrile, ethyl acetate, chloroform, toluene, carbon tetrachloride, n-heptane, iso-octane and n-nonane. The percentage yield of (−)-menthyl butyrate and enantioselectivity of each lipase used are shown in Table 5 and Table 6.

lower polarity (solvents with log P value higher than 3.50) could be due to lack of substrate and enzyme solubility. However, as shown in Table 5 and Table 6, percentage of enantiomeric excess were less affected by the polarity of the

TABLE 5

Activity of *Candida rugosa* Lipase as affected by various organic solvents on production of (−)-menthyl butyrate

| | | Yield of (−)-Menthyl Butyrate (%) | | | | | |
|---|---|---|---|---|---|---|---|
| Solvent | [a]Log P | Control | NL | EC | EC250L | XAD7 | HT |
| Acetonitrile | −0.33 | 0.8 ± 0.1 | 4.0 ± 0.6 | 9.4 ± 0.4 | 16.2 ± 2.8 | 15.8 ± 1.3 | 5.5 ± 0.7 |
| Ethyl acetate | 0.68 | 1.2 ± 0.0 | 5.8 ± 0.3 | 10.6 ± 0.8 | 22.9 ± 0.5 | 37.9 ± 0.5 | 37.0 ± 2.3 |
| Chloroform | 2.00 | 2.9 ± 0.0 | 5.7 ± 0.0 | 17.9 ± 3.5 | 26.5 ± 0.2 | 24.9 ± 0.7 | 31.6 ± 2.4 |
| Toluene | 2.50 | 4.9 ± 0.0 | 9.3 ± 2.9 | 18.9 ± 1.1 | 29.9 ± 1.2 | 35.3 ± 2.8 | 32.8 ± 8.6 |
| $CCl_4$ | 3.00 | 8.9 ± 0.3 | 5.8 ± 0.2 | 31.9 ± 1.4 | 41.9 ± 3.0 | 37.0 ± 1.5 | 35.5 ± 3.4 |
| Hexane | 3.50 | 8.5 ± 0.0 | 6.9 ± 0.6 | 33.9 ± 2.3 | 47.7 ± 4.2 | 60.1 ± 3.6 | 54.4 ± 0.6 |
| n-Heptane | 4.00 | 8.9 ± 0.1 | 6.2 ± 0.0 | 20.1 ± 0.5 | 29.1 ± 0.4 | 30.6 ± 0.9 | 39.5 ± 3.2 |
| Iso-Octane | 4.50 | 9.8 ± 0.3 | 5.6 ± 0.3 | 16.4 ± 0.2 | 25.8 ± 0.8 | 26.9 ± 0.9 | 32.1 ± 6.5 |
| n-Nonane | 5.10 | 6.5 ± 0.8 | 5.9 ± 0.4 | 15.4 ± 1.7 | 25.1 ± 0.2 | 33.2 ± 3.3 | 39.5 ± 1.9 |

[a]Log P is the logarithm of partition coefficient of a given solvent between water and 1-octanol.
Reactions were performed at 30° C. for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as mean ± standard deviation.

TABLE 6

Enantioselectivity of *Candida rugosa* lipase as affected by various organic solvents on production of (−)-menthyl butyrate

| | | ee (%) | | | | | |
|---|---|---|---|---|---|---|---|
| Solvent | [a]Log P | Control | NL | EC | EC250L | XAD7 | HT |
| Acetonitrile | −0.33 | 2.63 ± 1.37 | 10.87 ± 0.02 | 100 ± 0 | 100 ± 0 | 91.10 ± 0.32 | 85.04 ± 2.10 |
| Ethyl acetate | 0.68 | 2.30 ± 0.72 | 13.29 ± 3.26 | 100 ± 0 | 100 ± 0 | 100 ± 0 | 91.15 ± 0.47 |
| Chloroform | 2.00 | 0.37 ± 0.29 | 12.30 ± 0.22 | 100 ± 0 | 96.53 ± 0.14 | 93.63 ± 1.03 | 91.54 ± 0.11 |
| Toluene | 2.50 | 2.38 ± 0.13 | 10.63 ± 0.58 | 100 ± 0 | 100 ± 0 | 95.47 ± 0.49 | 89.65 ± 0.034 |
| $CCl_4$ | 3.00 | 2.51 ± 0.16 | 8.44 ± 0.72 | 100 ± 0 | 94.87 ± 1.74 | 96.89 ± 0.90 | 89.44 ± 0.08 |
| Hexane | 3.50 | 0.94 ± 0.19 | 13.54 ± 2.32 | 100 ± 0 | 94.79 ± 0.05 | 91.69 ± 0.62 | 81.51 ± 5.38 |
| n-Heptane | 4.00 | 2.76 ± 0.24 | 10.61 ± 0.01 | 100 ± 0 | 96.30 ± 0.32 | 95.27 ± 0.83 | 85.34 ± 0.77 |
| Iso-Octane | 4.50 | 2.54 ± 0.08 | 10.44 ± 0.01 | 100 ± 0 | 100 ± 0 | 94.94 ± 4.03 | 80.23 ± 0.85 |
| n-Nonane | 5.10 | 2.54 ± 0.09 | 10.09 ± 0.04 | 100 ± 0 | 100 ± 0 | 92.08 ± 0.04 | 81.77 ± 2.39 |

[a]Log P is the logarithm of partition coefficient of a given solvent between water and 1-octanol.
Reactions were performed at 30° C. for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as means ± standard deviation.

Higher yield and enantiomeric excess of (−)-menthyl butyrate were obtained by using immobilized *Candida rugosa* lipase compared to native *Candida rugosa* lipase. Hexane (log P=3.50) appeared to be the most suitable solvent. The decrease of product formed in solvents with higher polarity (solvents with log P value lower than 3.50) was due to the ability of the more polar solvent to strip off the water layer around the enzyme molecules, which is essential to preserve the spatial conformation of the enzyme. Decrease in percentage yield of (−)-menthyl butyrate synthesized in solvents with organic solvents and the immobilized lipases were very enantioselective as compared to native lipase.

EXAMPLE 2

Effect of temperature on *Candida rugosa* lipase activity was determined following the general procedure except that the reaction mixture was incubated at 40° C., 50° C., 60° C. and 70° C. aside from 30° C. The percentage yield of (−)-menthyl butyrate and enantioselectivity of each lipase used are shown in Table 7 and Table 8.

TABLE 7

Activity of *Candida rugosa* Lipase as affected by various temperatures on production of (−)-menthyl butyrate

| Temperature (° C.) | Yield of (−)-Menthyl Butyrate (%) | | | | | |
|---|---|---|---|---|---|---|
| | Control | NL | EC | EC250L | XAD7 | HT |
| 30 | 8.5 ± 0.0 | 6.9 ± 0.6 | 33.9 ± 2.3 | 47.7 ± 4.2 | 60.1 ± 3.6 | 54.3 ± 0.6 |
| 40 | 10.2 ± 0.0 | 6.7 ± 0.0 | 32.3 ± 0.3 | 46.9 ± 0.2 | 58.9 ± 1.6 | 50.2 ± 2.5 |
| 50 | 11.3 ± 0.6 | 5.6 ± 0.0 | 20.0 ± 1.1 | 44.8 ± 0.5 | 31.9 ± 0.8 | 50.2 ± 2.5 |
| 60 | 6.4 ± 0.0 | 5.5 ± 0.8 | 22.6 ± 1.2 | 31.5 ± 2.5 | 25.6 ± 1.7 | 37.2 ± 2.8 |
| 70 | 10.0 ± 1.5 | 5.2 ± 0.51 | 18.5 ± 2.7 | 24.8 ± 1.7 | 22.3 ± 0.0 | 37.2 ± 0.0 |

Reactions were performed in hexane for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as mean ± standard deviation.

TABLE 8

Enantioselectivity of *Candida rugosa* lipase as affected by various temperatures on production of (−)-menthyl butyrate

| Temperature (° C.) | ee (%) | | | | | |
|---|---|---|---|---|---|---|
| | Control | NL | EC | EC250L | XAD7 | HT |
| 30 | 0.94 ± 0.94 | 13.54 ± 2.32 | 100 ± 0 | 94.79 ± 0.05 | 91.96 ± 0.62 | 81.51 ± 5.38 |
| 40 | 1.99 ± 0.00 | 11.03 ± 2.56 | 100 ± 0 | 100 ± 0 | 93.89 ± 2.87 | 87.88 ± 0.23 |
| 50 | 1.88 ± 0.01 | 11.17 ± 0.11 | 100 ± 0 | 100 ± 0 | 95.70 ± 0.79 | 87.88 ± 0.23 |
| 60 | 1.64 ± 0.02 | 9.56 ± 0.19 | 100 ± 0 | 100 ± 0 | 92.30 ± 0.80 | 83.36 ± 0.04 |
| 70 | 1.67 ± 0.02 | 7.87 ± 0.55 | 93.75 ± 0.80 | 88.39 ± 0.49 | 92.77 ± 4.16 | 82.30 ± 0.00 |

Reactions were performed in hexane for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as means ± standard deviation.

*Candida rugosa* lipase immobilized on Eupergit® C 250 L and Mg—Al-Hydrotalcite-lipase were stable at temperatures between 30° C. to 50° C. while immobilized *Candida rugosa* lipase on Eupergit® C and Amberlite® XAD7 were stable at temperatures between 30° C. to 40° C.

EXAMPLE 3

Effect of water activity ($a_w$) on *Candida rugosa* lipase activity was determined following the general procedure except that the reaction mixture and lipase were pre-equilibrated with saturated salt solutions vapor of known water activity overnight prior incubation. Salt hydrates used were LiCl, $MgCl_2.6H_2O$, $Mg(NO_3)_2.6H_2O$, NaCl, KCl and $KNO_3$. The percentage yield of (−)-menthyl butyrate and enantioselectivity of each lipase used are shown in Table 9 and Table 10.

TABLE 9

Activity of *Candida rugosa* Lipase as affected by various water activities ($a_w$) on production of (−)-menthyl butyrate

| Salt Hydrate | $a_w$ | Yield of (−)-Menthyl Butyrate (%) | | | | | |
|---|---|---|---|---|---|---|---|
| | | control | NL | EC | EC250L | XAD7 | HT |
| LiCl | 0.11 | 7.8 ± 0.6 | 15.3 ± 0.6 | 17.6 ± 0.6 | 40.7 ± 1.9 | 23.2 ± 0.8 | 42.6 ± 3.2 |
| $MgCl_2.6H_2O$ | 0.33 | 8.4 ± 0 | 8.2 ± 0 | 36.2 ± 2.9 | 45.3 ± 2.1 | 43.4 ± 5.7 | 42.1 ± 1.0 |

TABLE 9-continued

Activity of *Candida rugosa* Lipase as affected by various water activities ($a_w$) on production of (−)-menthyl butyrate

| | | Yield of (−)-Menthyl Butyrate (%) | | | | | |
|---|---|---|---|---|---|---|---|
| Salt Hydrate | $a_w$ | control | NL | EC | EC250L | XAD7 | HT |
| Mg(NO$_3$)$_2$.6H$_2$O | 0.53 | 7.9 ± 0.2 | 11.5 ± 0.2 | 32.6 ± 0.1 | 41.0 ± 1.9 | 58.7 ± 2.3 | 38.4 ± 1.8 |
| NaCl | 0.75 | 9.1 ± 0.1 | 10.4 ± 0.1 | 26.7 ± 0.3 | 38.2 ± 3.0 | 25.4 ± 0 | 39.0 ± 0.0 |
| KCl | 0.86 | 7.4 ± 2.6 | 13.8 ± 2.6 | 18.1 ± 1.7 | 38.2 ± 1.0 | 27.2 ± 0.5 | 28.6 ± 0.7 |
| KNO$_3$ | 0.90 | 9.0 ± 0.7 | 7.1 ± 0.7 | 18.2 ± 0.7 | 38.3 ± 0.2 | 22.3 ± 1.0 | 28.2 ± 0.8 |

Reactions were performed in hexane at 30° C. for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as mean ± standard deviation.

TABLE 10

Enantioselectivity of *Candida rugosa* lipase as affected by various water activities ($a_w$) on production of (−)-menthyl butyrate

| | | ee (%) | | | | | |
|---|---|---|---|---|---|---|---|
| Salt Hydrate | $a_w$ | control | NL | EC | EC250L | XAD7 | HT |
| LiCl | 0.11 | 0.94 ± 0.16 | 11.94 ± 1.23 | 74.61 ± 0.23 | 80.57 ± 0.02 | 81.68 ± 0.03 | 70.28 ± 0.33 |
| MgCl$_2$.6H$_2$O | 0.33 | 0.33 ± 0.39 | 10.88 ± 0.31 | 74.28 ± 0.37 | 77.20 ± 0.06 | 78.56 ± 4.05 | 70.70 ± 1.60 |
| Mg(NO$_3$)$_2$.6H$_2$O | 0.53 | 1.00 ± 0.49 | 12.61 ± 0.17 | 73.65 ± 0.01 | 81.50 ± 0.01 | 84.25 ± 1.09 | 74.13 ± 0.00 |
| NaCl | 0.75 | 0.54 ± 0.07 | 10.06 ± 0.27 | 78.85 ± 2.87 | 81.19 ± 0.38 | 76.42 ± 0.06 | 79.03 ± 0.88 |
| KCl | 0.86 | 1.22 ± 0.56 | 12.04 ± 2.47 | 75.91 ± 1.15 | 81.74 ± 1.00 | 74.36 ± 0.15 | 72.90 ± 4.25 |
| KNO$_3$ | 0.90 | 1.09 ± 1.06 | 7.58 ± 0.24 | 74.32 ± 0.25 | 80.62 ± 0.20 | 81.84 ± 0.85 | 68.89 ± 0.50 |

Reactions were performed in hexane at 30° C. for 24 hours.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as means ± standard deviation.

Highest production of (−)-menthyl butyrate was obtained when immobilized *Candida rugosa* lipase on Eupergit® C or Eupergit® C 250 L was pre-equilibrated with salt hydrate having water activity value of 0.33 prior usage. On the other hand, immobilized *Candida rugosa* lipase on Amberlite® XAD7 showed highest activity when it was pre-equilibrated with salt hydrate having water activity value of 0.53 prior usage. *Candida rugosa* lipase immobilized on Mg—Al-hydrotalcite exhibited highest activity when it was pre-equilibrated with salt hydrate having water activity value within the range of 0.11 to 0.33 prior usage.

EXAMPLE 4

Time course for production of (−)-menthyl butyrate using native *Candida rugosa* lipase and immobilized *Candida rugosa* lipase on Eupergit® C, Eupergit® C 250 L, Amberlite® XAD7 and Mg—Al-Hydrotalcite are shown in Table 11. The production of menthyl butyrate was conducted according to the general procedure and product samples were taken at various intervals.

TABLE 11

Yield of (−)-menthyl butyrate at various reaction period

| Time | Yield of (−)-MenthylButyrate (%) | | | | |
|---|---|---|---|---|---|
| (hour) | NL | EC | EC250L | XAD7 | HT |
| 0 | 0 | 0 | 0 | 0 | 0 |
| 0.25 | 1.96 | 8.37 | 8.53 | 23.53 | 5.18 |
| 0.50 | 2.35 | 12.48 | 13.28 | 28.19 | 9.71 |
| 1.00 | 2.52 | 14.30 | 17.45 | 33.70 | 14.00 |
| 2.00 | 3.02 | 15.70 | 21.00 | 38.10 | 19.60 |
| 3.00 | 3.17 | 18.30 | 24.25 | 41.30 | 25.56 |
| 4.00 | 3.87 | 21.40 | 28.20 | 43.60 | 31.00 |
| 5.00 | 4.29 | 23.80 | 30.80 | 46.00 | 36.8 |
| 6.00 | 4.33 | 25.60 | 33.70 | 48.30 | 40.20 |
| 7.00 | 5.83 | 27.70 | 36.00 | 50.90 | 43.60 |
| 8.00 | 6.88 | 30.30 | 39.20 | 53.80 | 47.00 |
| 12.00 | 7.93 | 32.40 | 42.00 | 57.58 | 51.30 |
| 24.00 | 9.00 | 34.70 | 44.10 | 59.21 | 54.79 |
| 28.00 | 9.87 | 34.70 | 43.40 | 59.80 | 54.60 |
| 30.00 | 11.56 | 32.60 | 41.30 | 60.51 | 53.80 |

TABLE 11-continued

Yield of (−)-menthyl butyrate at various reaction period

| Time (hour) | Yield of (−)-MenthylButyrate (%) | | | | |
|---|---|---|---|---|---|
| | NL | EC | EC250L | XAD7 | HT |
| 32.00 | 11.80 | 29.50 | 38.10 | 60.90 | 51.20 |
| 52.00 | 12.01 | 26.62 | 35.00 | 61.48 | 49.10 |
| 54.00 | 12.18 | 25.05 | 31.60 | 62.20 | 47.84 |
| 58.00 | 12.77 | 24.33 | 29.70 | 63.20 | 47.83 |
| 60.00 | 13.49 | 24.24 | 29.10 | 65.95 | 47.80 |

Reactions were performed in hexane at 30° C.
Control = without enzyme,
NL = native lipase,
EC = Eupergit ® C-lipase,
EC250L = Eupergit ® C 250 L-lipase,
XAD7 = Amberlite ® XAD7-lipase,
HT = Mg—Al-Hydrotalcite-lipase.
The values are reported as mean ± standard deviation.

At 30° C., percentage yield of (−)-menthyl butyrate increased rapidly within four to six hours and continuous production of (−)-menthyl butyrate was observed even after about 60 hours of reaction when immobilized *Candida rugosa* lipase on Amberlite® XAD 7 was used to catalyze the reaction. When immobilized *Candida rugosa* lipase on Eupergit® C 250 L, Eupergit® C or Mg—Al-hydrotalcite was used, percentage yield of (−)-menthyl butyrate reached an optimum yield of 44%, 35% and 55% respectively at 24 hours of incubation. At this point, the reaction may have reached its equilibrium state. Production of (−)-menthyl butyrate was found to decrease thereafter. Reaction with native lipase however takes about 60 hours to convert (−)-menthol to about 13% of ester. Immobilized enzyme seemed to increase enantioselective esterification activity of lipase by six to seven folds compared to native lipase.

The invention claimed is:

1. An immobilized lipase for enantioselective esterification reaction which comprises a lipase from *Candida rugosa* immobilized on Mg—Al-hydrotalcite.

2. A method of resolving racemic alcohols and/or carboxylic acids, which comprises:
contacting a lipase from *Candida rugosa* immobilized on Mg—Al-hydrotalcite with racemic alcohols, carboxylic acids and/or esters thereof.

3. A method of resolving racemic alcohols and/or carboxylic acids, which comprises:
subjecting racemic alcohols and/or carboxylic acids to enantioselective esterification in the presence of a lipase from *Candida rugosa* immobilized on Mg—Al-hydrotalcite to produce a mixture of esters in which the esters of the desired enantiomer is in enantiomeric excess; and hydrolyzing the mixture of esters.

* * * * *